US005458612A

United States Patent [19]
Chin

[11] Patent Number: 5,458,612
[45] Date of Patent: Oct. 17, 1995

[54] PROSTATIC ABLATION METHOD AND APPARATUS FOR PERINEAL APPROACH

[75] Inventor: Albert K. Chin, Palo Alto, Calif.

[73] Assignee: Origin Medsystems, Inc., Menlo Park, Calif.

[21] Appl. No.: 178,063

[22] Filed: Jan. 6, 1994

[51] Int. Cl.$^6$ ................................................. A61M 31/00
[52] U.S. Cl. .................................................. 606/192
[58] Field of Search ................................. 604/96, 49, 53, 604/101, 54; 606/192–196

[56] References Cited

U.S. PATENT DOCUMENTS

| | | |
|---|---|---|
| 4,762,128 | 8/1988 | Rosenbluth . |
| 4,810,247 | 3/1989 | Glassman ................................ 604/171 |
| 4,893,623 | 1/1990 | Rosenbluth . |
| 5,007,898 | 4/1991 | Rosenbluth et al. ..................... 604/101 |
| 5,029,584 | 7/1991 | Smith ...................................... 604/28 |
| 5,188,596 | 2/1993 | Condon et al. .......................... 606/192 |
| 5,190,046 | 3/1993 | Shturman ................................ 604/96 |
| 5,209,725 | 5/1993 | Roth ........................................ 606/191 |
| 5,271,383 | 12/1993 | Wilic ...................................... 604/96 |
| 5,316,016 | 5/1994 | Adams et al. ........................... 604/96 |
| 5,330,490 | 7/1994 | Wilic et al. ............................. 604/96 |

FOREIGN PATENT DOCUMENTS

| | | | |
|---|---|---|---|
| 8303188 | 9/1983 | WIPO ................................. 606/7 |
| 9210142 | 6/1992 | WIPO ................................. 606/7 |

OTHER PUBLICATIONS

Paul H. Lange, M.D., "Diagnostic and Therapeutic Urologic Instrumentation" (Chapter 8, pp. 510–540).
Rudolf M. Verdaasdonk, Cornelius Borst, "Modified Fiber Tips: Optical and Thermal Characteristics".
John T. Isaacs, Ph.D., Gary D. Steinberg, M.D., *Contemporary Urology* (May 1990), "A Guide to the Physiology of the Prostate" (pp. 54–68).
Prostatism (p. 826).
Karl Storz—Endoskope Brochure "Cystoscopy–Urethroscopes" Cyst 1A.
Surgical Anatomy of the Perinaeum (pp. 1063–1069).
Christopher M. Dixon, M.D., Herbert Lepor, M.D., *Contemporary Urology* (Oct. 1993), "Lasers Add a Glow to the Search for BPH Therapies" (pp. 44–62).

Primary Examiner—C. Fred Rosenbaum
Assistant Examiner—Manuel Mendez
Attorney, Agent, or Firm—Fulwider Patton Lee & Utecht

[57] ABSTRACT

The invention is directed to a novel method and apparatus for treatment of a diseased internal organ, specifically, the male prostrate gland. The method and apparatus are specific to a transperineal approach to the prostate gland. The apparatus comprises a catheter containing a plurality of lumens therethrough, an inflatable transparent member in fluid communication with one of the lumens and placed on the distal end of the catheter, and visualizing means to allow for visualization of the area to be treated through said inflatable member. Upon inflation, the inflatable member aids in the separation of the prostrate gland from the rectal wall. Additionally, treating means can be inserted through another of the lumens in order to obtain the desired systemic effect on the prostate gland.

4 Claims, 2 Drawing Sheets

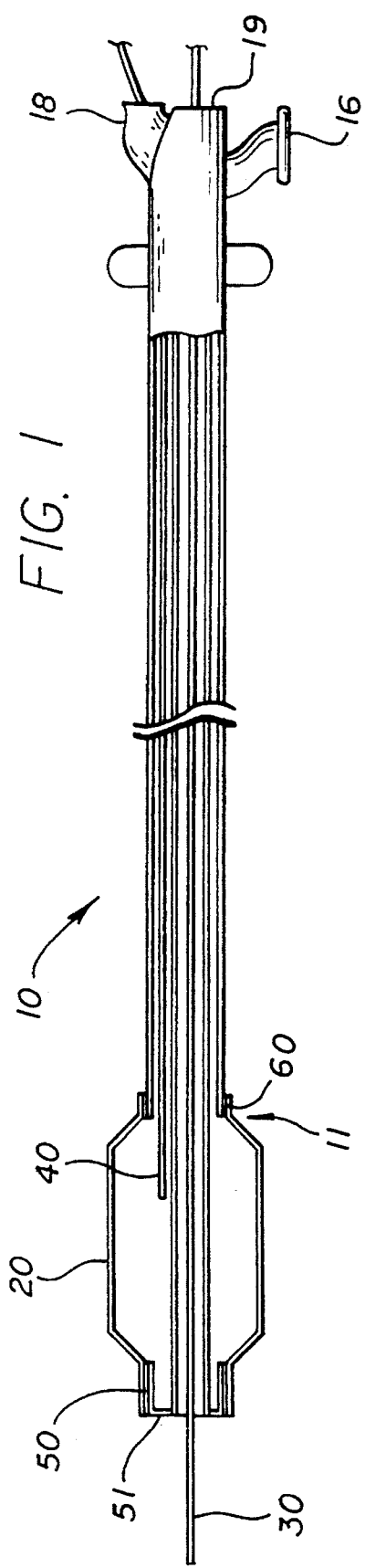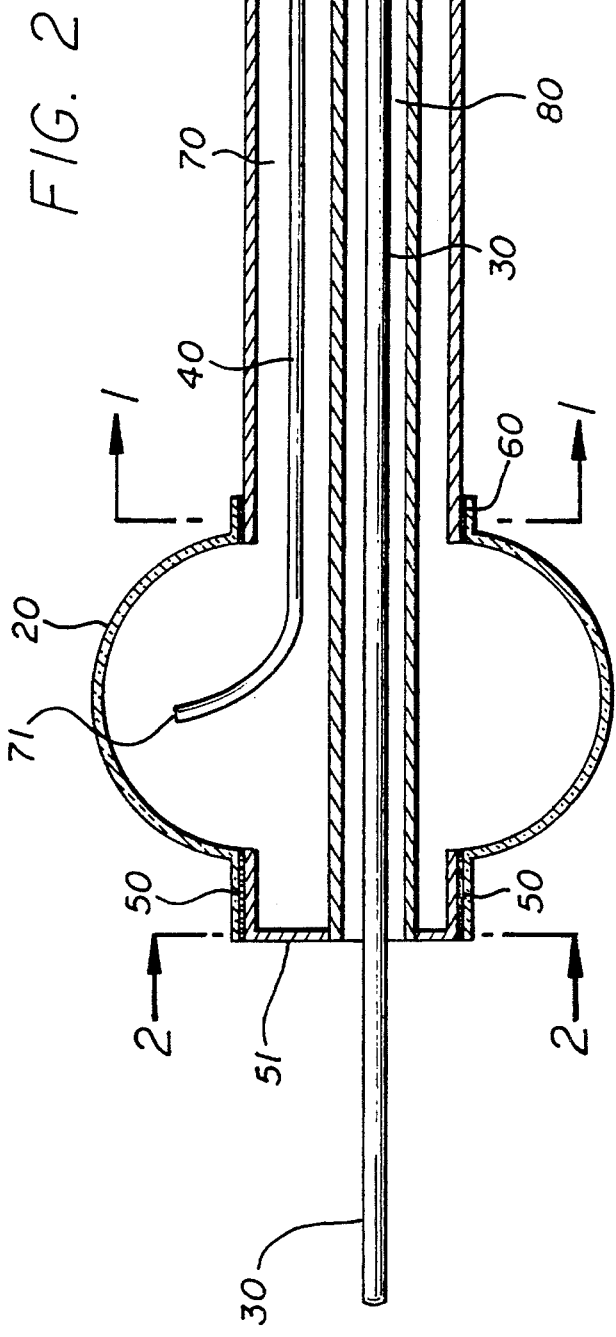

PROSTATIC ABLATION METHOD AND APPARATUS FOR PERINEAL APPROACH

BACKGROUND OF THE INVENTION

This invention relates to a method and apparatus for ablating all or part of a human interior organ. More particularly, the invention relates to a device and method for performing a complete or partial prostatectomy of a diseased prostrate gland in the human male.

The need for treatment of the prostate gland is important for several reasons. These include maintaining the patency of the prostatic urethra allowing for adequate urinary outflow, reducing urinary tract infections, treating hematuria, treating malignancy, and treating renal insufficiency. It is estimated that 50% of men over the age of 50 have some type of benign prostatic hyperplasia of the prostate with that percentage increasing significantly with age.

There are numerous treatment methods well known in the art for the treatment of the prostate gland which includes, but is not limited to: an open surgical method for direct access to the gland whereby the excision occurs retropubically or transperineally; a transurethral method whereby a device is inserted through the urethra followed by any number of treatment methods; and more recently, pharmacological agents that relax the smooth musculature of the prostate thereby reducing prostatic size.

One of the more common clinical methods of treating the prostrate is transurethral insertion of a device for access to the prostate. Treatment and/or detection methods may include balloon dilation on a catheter, placement of permanent or temporary stents to stabilize the diameter of the urethra, cryotherapy, laser ablation or thermal therapy to reduce the size of the prostate, or heated wire loop or cutting edge used to cut away prostatic tissue. The disadvantages of the transurethral approach are damage to the urethral endothelium and severe patient discomfort.

In the open surgical retropubic method, an incision is made superior to the penis in the abdominal region to expose the bladder and the prostate gland. The clinician subsequently removes all or a portion of the prostatic tissue by hand, cauterizes any bleeding vessels and passes a catheter through the urethra to temporarily drain urine from the bladder. This type of invasive surgery, generally requiring a hospital stay of several days, has many possible complications and is not used unless the prostrate gland has enlarged to an extent whereby transurethral or pharmacological agents would be difficult or have little systemic effect on the gland. Other surgical methods include the transrectal approach or a transperineal approach. In the transrectal method the prostate is accessed through the rectal wall. The patient must be placed on antibiotics at least 24 hours prior to surgery to reduce any chance of post operative infection. Additionally, enemas should be given prior to surgery to eliminate any fecal matter that may be posited in the lower rectal cavity and be transmitted into the perineal cavity contaminating the procedure with enteric bacterial seeding. This approach has a higher degree of infection and traumatic complications such as hemorrhage or urinary retention than other methods.

The transperineal approach accesses the prostate through the perineum and is not frequently used because of the difficulty in verifying the exact location of the treatment device within the prostrate. Additionally, rupture of the prostatic urethra and/or the rectal wall often has been a major problem during manipulation. Recently, an attempt has been made to decrease this blind manipulation by utilizing a rectal ultrasound probe to aid in the guidance of a marked needle through the perineal tissue. This procedure does not utilize direct vision and is time sensitive.

What has been needed yet heretofore unavailable is a safe and effective method to easily and cost effectively access the prostate gland so that it causes minimal trauma to the patient and yet still be effective and suitable. The present invention fulfills these needs.

SUMMARY OF THE INVENTION

Generally, the present invention provides a novel method and apparatus to treat the prostate gland via perineal insertion of a catheter, including direct visualization of the area to be treated and treating means. Atraumatic separation of the prostate gland from the adjacent rectal wall is facilitated by the use of an inflatable member. Additionally, this method does not have the same symptomatic risks of transurethral, transrectal, or retropubic access to the prostrate gland as discussed above.

Briefly, the novel method of prostatic ablation involves infiltrating the skin anterior to the anal opening with a local anesthesia and making an incision to allow catheter entry. A catheter of the invention is then inserted into the perineal tissue so that the inflatable member is positioned between the prostate gland and the rectal wall. The inflatable member is then inflated via a balloon inflation port in order to aid in the separation of perineal tissue and to separate the prostate gland from the rectal wall. A fiberoptic scope is housed within a scope lumen to aid in visualizing the separation of the prostate gland from the rectal wall with minimal trauma to the perineal tissue. A fiberoptic scope is also used to aid in the visualization of the procedure including visualizing the location of the distal tip of the catheter. The fiberoptic scope is inserted through the scope lumen and it projects slightly into the inflatable member which is transparent. The fiberoptic scope assists in visualizing the location of the distal end of the catheter and the area surrounding the transparent inflatable member.

After the prostate gland has been separated from the rectal wall by the inflatable member, any one of a number of treating means may be inserted through a treating lumen in the catheter which allows direct access to the prostrate gland. This is accomplished by placing the distal tip of the catheter in direct contact with the prostate gland. At this point the treating means inserted through the treating lumen would extend directly into the prostate gland by extending it beyond the distal tip of the catheter directly into the prostrate gland. The treating means can include any one of a number of methods known in the art to aid in the treatment of the prostate including, but not limited to laser ablation, cryotherapy, needle insertion, aspiration, heated wire loop, blade type carving, and resection.

These and other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a schematic view of the catheter of the invention prior to insertion.

FIG. 2 is a partial schematic view of the catheter of FIG. 1 where the inflatable member is in an expanded state.

DETAILED DESCRIPTION OF THE PREFERRED EMBODIMENTS

The present invention includes treatment of benign prostatic hypertrophy by prostatic ablation techniques. The present invention includes an apparatus and method using a perineal approach for treating the prostrate gland so that a less traumatic and more effective treatment procedure is utilized.

Figure 3:
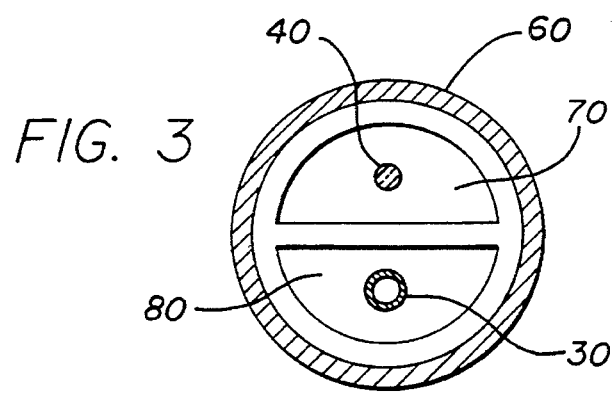
FIG. 3 is a cross sectional view taken along line 1—1 in FIG. 2 depicting the lumens of the catheter.
Figure 4:
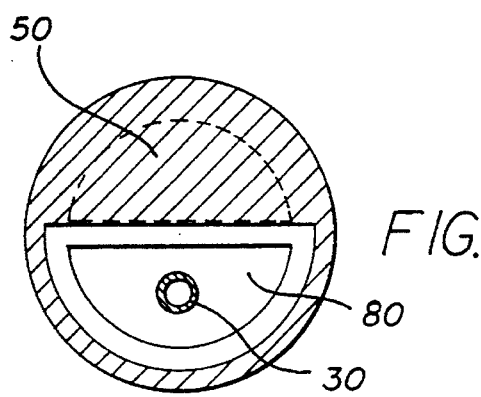
FIG. 4 is a cross sectional view taken along line 2—2 in FIG. 2 depicting the distal tip of the catheter.

In a preferred embodiment, as shown in FIGS. 1–4, a catheter shaft 10, which is approximately 20 cm in length and between 3.5 and 4 mm diameter, includes a scope lumen 70 and a treating lumen 80 extending the length of the catheter shaft. The catheter itself can be manufactured from any one of a number of materials known in the art including polycarbonate, polyvinylchloride or stainless steel hypotubing.

Near the distal portion 11 of catheter shaft 10 is an inflatable member 20 which can be a balloon formed of silicone, polyurethane, or latex, all of which should be capable of about five hundred percent expansion and having a spherical or cylindrical configuration disposed about the distal end of catheter shaft 10 when expanded. The balloon 20 is attached to the distal portion 11 of the catheter at distal tip 50 while the proximal end of the balloon 20 is attached to catheter shaft 10 at point 60. The attachment means located at areas 50 and 60 do not normally exceed 3–5 mm in length along the catheter shaft, and generally can be any type of adhesive that is well known in the art. The balloon can inflate to about 5 cc, which is an amount to make it sufficiently rigid to aid in separation of the perineal tissues and the prostrate gland from the rectal wall. Importantly, balloon 20 is transparent so that a visualizing means within the balloon can be used to view inside and outside the balloon.

Catheter shaft 10 houses a pair of lumens and is commonly referred to as a dual lumen catheter. A scope lumen 70 and a treating lumen 80 extend along the catheter shaft, from the proximal end toward the distal end of the shaft 10. The scope and treating lumens of the catheter end respectively in airtight valves 18 and 19 at the proximal end of the catheter. The valves may be composed of elastomeric membranes covering the entrance into the lumens, or they may be Tuohy-Borst type O-ring seals commonly used in radiologic catheters.

Scope lumen 70 acts both as an inflation lumen for the balloon 20 and as a housing for a fiber optic scope 40. The fiber optic scope 40 is used to visualize the placement of a treating means 30 as it is inserted into the prostate gland. As can be seen from the drawing figures, scope lumen 70 terminates approximately 5–10 mm proximally to the distal tip 51 of catheter shaft 10. The scope lumen generally terminates near the proximal end of balloon 20 where it is attached at attachment point 60 on the catheter shaft.

It is intended that when the fiber optic scope 40 is inserted into and threaded through scope lumen 70, the distal tip 71 of the fiber optic scope exits the distal tip of scope lumen 70 and extends into balloon 20. With the tip of the fiber optic scope 40 extending into the balloon area, it can adequately visualize the balloon area and the surrounding tissue, since balloon 20 is transparent. Further, fiber optic scope 40 is used to visualize the distal end of the catheter shaft 10 as it is being inserted through the perineum and as it is being positioned prior to balloon inflation in the location between the prostate and the rectal wall.

The treating lumen 80 extends from the proximal end of catheter shaft 10 to its distal end, thereby providing a continuous and unobstructed through lumen. The treating lumen 80 allows for the advancement of a treating means 30 so that the treating means can exit the distal tip of catheter shaft 10 and come into direct contact with the prostate gland. The amount of advancement through the treating lumen 80 depends on the type of treating means used for a particular patient. The treating means 30 does not usually exceed 2 cm beyond the distal tip of catheter shaft 10 so as to avoid complete puncture of the gland and a possible rupture through the urethra or the rectal wall.

In a preferred embodiment, a hollow needle 30 is advanced through the through lumen 80 and into the prostate gland. An energy probe may then be introduced into the prostate via the hollow needle 30 in order to treat the prostate gland. Alternative embodiments of the treating means 30 are known in the art and can include laser ablation, pharmacological agents, cryotherapy, thermotherapy, blade carving, heated wire loops, and so forth. The treating means may be withdrawn and the catheter tip manipulated in order to treat different areas or lobes of the prostate where necessary. Generally, in about eighty percent of the cases, the lateral lobe of the prostate gland will require medical treatment, thus the catheter placement will most often be in the lateral lobe area.

The novel method of the invention comprises the insertion of the catheter through the perineum in order to treat the prostrate gland by isolating the gland from the rectal wall.

Figure 5:
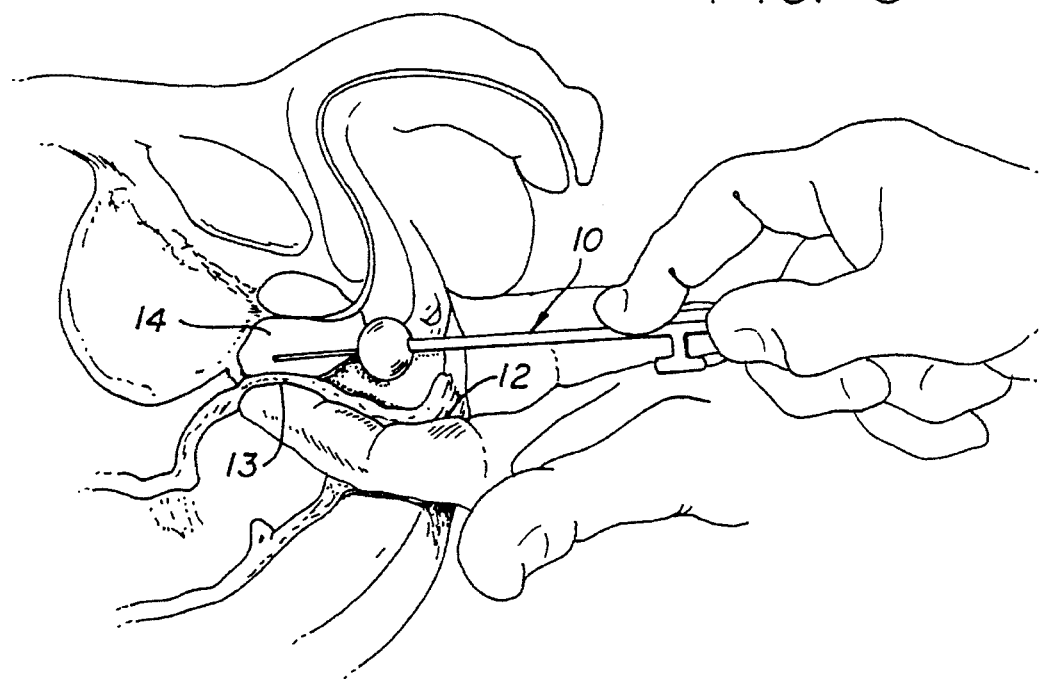
FIG. 5 is a mid-sagittal view of the male pelvis demonstrating a method of inserting the catheter and treating means by insertion through the perineum.

Referring to FIGS. 1–5, there is illustrated a method of the invention which, in this embodiment, comprises making an incision approximately 3–5 mm anterior to the anal opening 12 in the ischio-rectal region of the human male. The incision should be large enough to allow insertion of catheter 10. The path of insertion of the catheter separates the muscular and fatty tissues between the bulbospongiosus and the rectal wall and traverses the perineal membrane. Upon insertion of the catheter, the fiber optic scope 40 can be used to a limited degree in order to differentiate fatty or muscular tissue as the catheter is negotiated towards the prostrate gland by the clinician. Further, the clinician may insert a finger in the rectum to feel the location of the catheter as it is being positioned and to insure that the catheter does not puncture the rectal wall. The clinician may also use some form of ultrasound during the insertion and location steps of the procedure to enhance the ability to visualize the catheter and balloon portion.

When the inflatable member 20 is positioned between the prostate gland 14 and the rectal wall 13, it is inflated via balloon port 16 which is in fluid communication with scope lumen 70. In a preferred embodiment, the inflation fluid is air so that the interior of the inflatable member 20 is unobstructed for using the fiber optic scope 40. As the inflatable member 20 expands, it will separate the prostate gland from the rectal wall thereby isolating the prostate gland, and insuring that the distal tip of the catheter does not traumatize the rectal wall. Since the inflatable member 20 is transparent, the fiber optic scope 40 can be utilized to assist in locating the inflatable member with respect to the prostate gland and the rectal wall, and can assist in visualizing the distal tip of the catheter and its position relative to the prostate gland.

Once the prostrate has been atraumatically separated from the rectal wall, the distal tip of the catheter can be maneuvered with the help of the visualizing means (fiber optic scope), to be positioned on the surface of the prostate gland. Treating means 30 can be inserted into the through lumen 80 past the distal tip of the catheter into the gland itself. As discussed previously, treating means can be any one or a combination of means known in the art to have a systemic effect on the prostrate. The catheter tip can be subsequently repositioned in the same or different lobes of the prostrate and the treating means reinserted into the gland in order to fully treat the gland. After treatment the inflatable member is deflated and catheter withdrawn.

While several particular forms of the invention have been illustrated and described, it will be apparent that various modifications can be made by one skilled in the art without departing from the spirit and scope of the invention. For example, while several preferred materials or certain dimensions have been referenced, they are by way of example and not meant to be limiting. Accordingly, the scope of the invention is intended to be defined only by reference to the appended claims.

What is claimed is:

1. A method of treating the prostate gland, comprising the steps of:

providing a catheter having a transparent inflatable member in fluid communication with a scope lumen, said catheter also having a treating lumen;

incising an area in the ischio-rectal region;

inserting said catheter through said incision and into and through the perineum;

positioning said inflatable member between the prostate gland and the rectal wall;

inflating said inflatable member to separate the prostate gland from the rectal wall;

visualizing means for visualizing within and outside of said inflated transparent inflatable member to assist in positioning a distal end of said catheter relative to said prostate gland; and inserting a treating means through said treating lumen and extending distally of said catheter distal end to contact and provide medical treatment to the prostate gland.

2. The method of claim 1, wherein said incision is made approximately 3–5 mm anterior to the anal opening in the ischio-rectal region.

3. The method of claim 1, wherein said inflatable member is deflated after the prostate gland has been medically treated and said catheter is withdrawn from said incision.

4. A method of treating the prostate gland, comprising the steps of:

providing a catheter having a transparent inflatable member in fluid communication with a scope lumen, said catheter also having a treating lumen;

incising an area in the ischio-rectal region;

inserting said catheter through said incision and into and through the perineum;

positioning said inflatable member between the prostate gland and the rectal wall;

inflating said inflatable member to separate the prostate gland from the rectal wall;

visualizing means for visualizing within and outside of said inflated transparent inflatable member to assist in positioning a distal end of said catheter relative to said prostate gland;

inserting a treating means through said treating lumen and extending distally of said catheter distal end to contact and provide medical treatment to the prostate gland;

withdrawing said treating means into said treating lumen;

repositioning said catheter distal end to contact a different portion of the prostate gland; and reinserting said treating means through said treating lumen and extending distally of said catheter distal end to contact and provide further medical treatment to the prostate gland.

\* \* \* \* \*